United States Patent [19]

Hamlin et al.

[11] Patent Number: 5,009,659
[45] Date of Patent: Apr. 23, 1991

[54] FIBER TIP ATHERECTOMY CATHETER

[75] Inventors: Robert N. Hamlin, Stillwater; Rick L. Shockey, Eagan; Robert A. V. Tassel, Excelsior, all of Minn.

[73] Assignee: Schneider (USA) Inc., Minneapolis, Minn.

[21] Appl. No.: 428,885

[22] Filed: Oct. 30, 1989

[51] Int. Cl.[5] .............................................. A61B 17/32
[52] U.S. Cl. .................................... 606/159; 606/180; 606/194; 30/276
[58] Field of Search .................... 604/22, 96; 606/159, 606/167, 180, 191, 194, 170; 128/755; 15/72, 104.14; 30/276

[56] References Cited

U.S. PATENT DOCUMENTS

| | | | |
|---|---|---|---|
| 1,837,904 | 12/1931 | Hawlet | 15/104.14 |
| 2,712,823 | 7/1955 | Kurtin | 606/180 |
| 3,492,684 | 2/1970 | Altemare | 15/104.14 |
| 3,831,278 | 8/1974 | Voglesonger | 30/276 |
| 4,784,636 | 11/1988 | Rydell | |
| 4,848,342 | 7/1989 | Kaltenbach | 606/194 |
| 4,886,061 | 12/1989 | Fischell et al. | 606/159 |
| 4,895,560 | 1/1990 | Papantonakos | 606/159 |
| 4,909,781 | 3/1990 | Husted | 606/159 |
| 4,966,604 | 10/1990 | Reiss | 606/159 |

Primary Examiner—Stephen C. Pellegrino
Assistant Examiner—Ralph A. Lewis
Attorney, Agent, or Firm—Haugen and Nikolai

[57] ABSTRACT

A catheter assembly especially designed for the performance of atherectomy procedures which include an elongated flexible plastic tube which can be routed through the vascular system to the location of the atheroma to be removed and a working catheter insertable through the guide catheter in the form of an elongated flexible plastic tube having a series of fibers integrally formed with or otherwise attached to the distal end portion of the working catheter and normally laying flat against the wall of the catheter. The proximal end of the working catheter is adapted for connection to a high speed motor whereby the working catheter can be rotated relative to the surrounding guide catheter. As the distal end portion of the working catheter is advanced distally beyond the end of the guide catheter, centrifugal force acts upon the fibers to cause them to extend radially outward from the core of the working catheter and when advanced against an atheroma, flail the lesion, reducing it small particles which can be aspirated out the proximal end of the catheter assembly.

5 Claims, 1 Drawing Sheet

U.S. Patent  Apr. 23, 1991  5,009,659
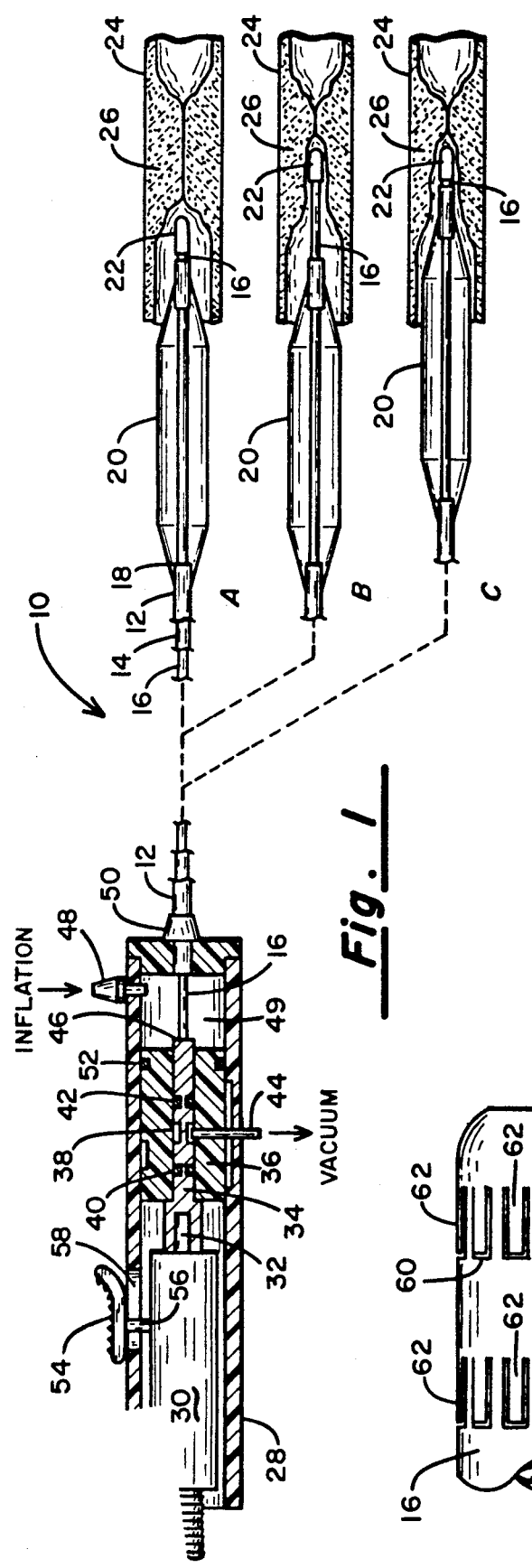
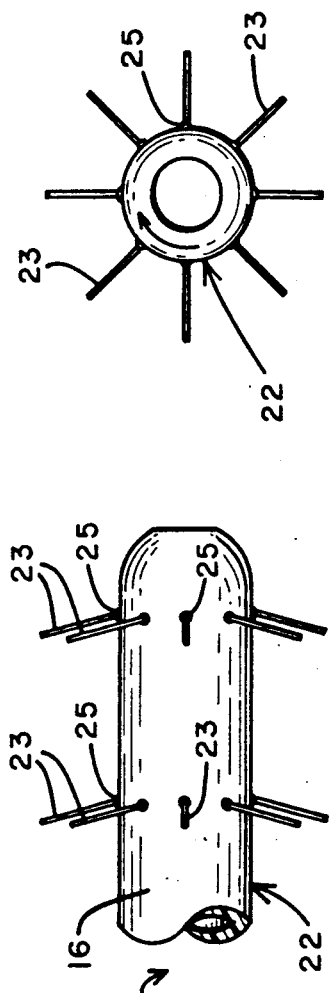
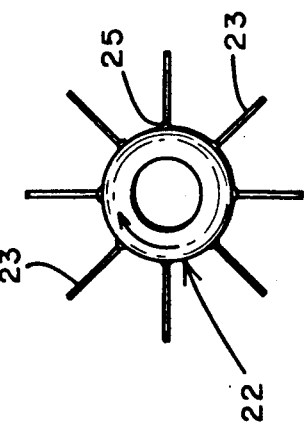
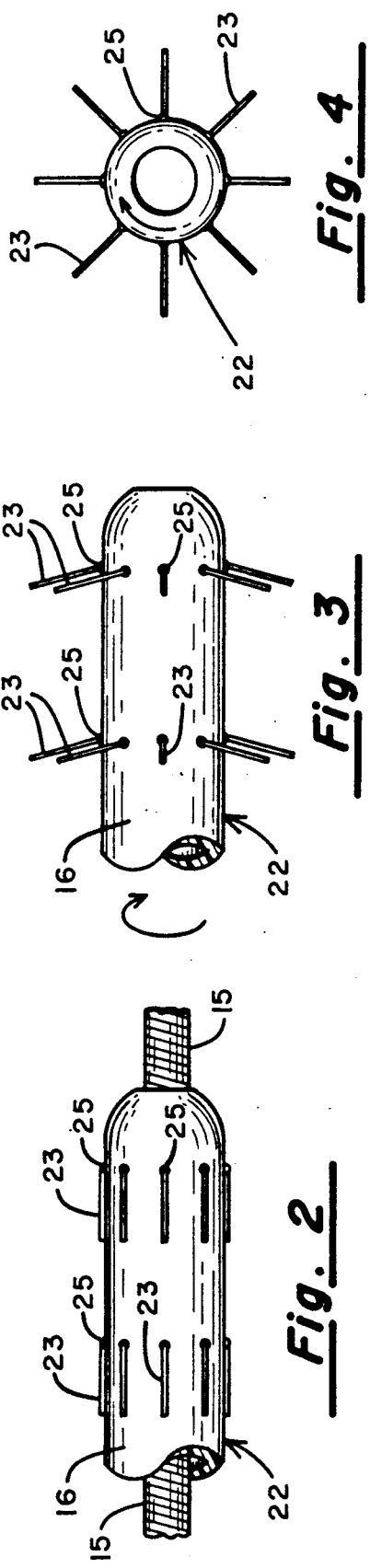

FIBER TIP ATHERECTOMY CATHETER

BACKGROUND OF THE INVENTION

I. Field of the Invention

This invention relates generally to medical apparatus for removing plaque and other deposits from the interior walls of a partially occluded blood vessel, and more particularly to the design of an atherectomy catheter whose cutting head exhibits a low profile to facilitate its being routed through the vascular system but which expands in use to effect removal of the atheroma.

II. Discussion of the Prior Art

The buildup of atheromas or the formation of thrombi in a blood vessel can cause serious circulatory problems and when complete blockages occur, distal tissues may be deprived of oxygen and nutrients leading to death of those cells distally of the blockage. Thus, the formation of an atheroma in a coronary artery can lead to a coronary infarction, especially when the artery becomes so narrowed by the plaque build-up that a tiny clot or thrombus cannot pass. Similarly, an atheroma or other type of stenotic lesion in a peripheral vein or artery can have a corresponding affect on tissue and cells supplied by the blocked blood vessel.

The treatment of such a condition naturally depends upon the location or site of the blockage. In the case of a blocked or partially blocked coronary artery, it has been the practice to conduct open-heart surgery wherein the blocked vessel is by-passed with an autograft. Similarly, blood vessel shunts have been installed in other body areas as well. Such surgery, however, tends to be quite traumatic involving opening the patient's chest and pericardium in the case of coronary by-pass surgery or extensive excision and vessel replacement in the case of other peripheral blockages.

More recently, following the technique created by A. Grunzig, a balloon catheter may be used to restore patency to a blood vessel without extensive surgery. A catheter having a small inflatable balloon on its distal end may be routed through the vascular system to the site of the constriction or blockage and when the deflated balloon is appropriately positioned to span the blockage, a fluid may be introduced into the proximal end of the catheter to inflate the balloon to a sufficiently high pressure whereby the blockage may be spread open and patency restored.

As in pointed in the Auth U.S. Pat. No. 4,445,509, there are certain deficiencies in the Grunzig procedure which render it ineffective in certain applications. For example, the blockage may be such that it is not possible to safely force the distal tip of the catheter through the blockage prior to the inflation of the balloon. In such a situation, it would be desirable if one could safely "tunnel" through the blockage using an appropriate cutting tool. Once a passage has been formed during such tunneling operation, a balloon can be advanced into the occlusion until it is totally across it. Once so positioned, the balloon can be inflated and the angioplasty procedure completed.

In U.S. Pat. No. 4,784,636 to Rydell and assigned to applicant's assignee, there is described a balloon atherectomy catheter comprising three concentrically disposed flexible plastic tubes. The innermost tube has an annular cutter secured to its distal end and secured to the proximal end of that catheter is a device which allows both rotational and translational motion to be imparted to that innermost tube. The cutter member is especially designed to preferentially remove tissue deposits directly in line with the cutter without producing significant lateral cutting.

SUMMARY OF THE INVENTION

The present invention provides an improved working catheter which may be used in place of the innermost catheter illustrated and described in the aforementioned Rydell U.S. Pat. No. 4,784,636. It includes an elongated tubular flexible shaft made of stainless steel or a polymeric material having a proximal end and distal end. The cutting head on the distal end portion of the tubular body comprises a plurality of fibers which are either integrally formed in the surface of the tube by slitting the tube or, alternatively, may be separate elements which are bonded to the outer periphery of the tube at one end only and arranged to lay flat along the exterior wall of the innermost tube and thus present a low profile during the catheterization process. When the working catheter is advanced in the distal direction such that the distal end thereof projects outwardly beyond the surrounding guide catheter, and when the shaft of the working catheter is driven at high speeds, centrifugal force causes the fiber elements at the distal end thereof to project radially outwardly to flail and thereby pulverize the stenotic lesion. When the motor is again stopped, the fibers will again lay down against the periphery of the working catheter's shaft as the working catheter is pulled back into the guide catheter.

OBJECTS

It is accordingly a principal object of the present invention to provide an improved apparatus and technique for treating vascular atheromas.

Another object of the invention is to provide a working catheter for use in a guide catheter having fiber elements at the tip thereof which are made to project radially outward upon high speed rotation of the catheter shaft.

These and other objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE DRAWINGS

FIG. 1A illustrates by means of a partially sectioned view the preferred embodiment of the invention with the cutter head in its retracted, stopped position;

FIG. 1B is a partial view showing the cutter in its extended position while being driven;

FIG. 1C is a partial view of the catheter of the present invention at a further step in the process;

FIG. 2 is a side view of the distal end portion of the working catheter when stationary;

FIG. 3 is a side view of the cutter tip when being driven;

FIG. 4 is an end view of FIG. 3; and

FIG. 5 illustrates the manner in which the cutting fibers may be integrally formed with the shaft of the working catheter.

DESCRIPTION OF THE PREFERRED EMBODIMENT

Referring to FIG. 1A, the atherectomy catheter assembly of the present invention is indicated generally by numeral 10 and is seen to include three concentrically disposed elongated flexible tubular plastic members 12, 14 and 16. The outer tubular member 12 has a distal end portion 18 to which is sealingly affixed an inflatable expander member 20 which may preferably be formed from a thin biaxially oriented plastic such as polyethylene terephthalate (PET) or another suitable plastic. As can be seen in FIG. 1A, the distal end of the intermediate tubular member 14 projects beyond the distal end 18 of the outer tubular member 12 and the distal end of the expander 20 is sealed to the outer periphery thereof. As will be further explained, this will permit an inflation fluid to be injected through the lumen of the outer tube 12 and into the confines of the expander member 20. The expander 20 can subsequently be deflated by aspirating the inflation fluid out from the proximal end of the catheter assembly.

The innermost catheter 16, which is also referred to herein as the drive or working catheter, is configured to pass over a guidewire and fits loosely within the lumen of the intermediate tube 14. Its distal end can be made to extend outwardly beyond the distal end of the intermediate catheter, all as shown in FIG. 1A.

As shown in FIGS. 2 through 4, the distal end portion 22 of the innermost working catheter 16 disposed on a guidwire 15 is provided with a plurality of elongated fibers as at 23, it being recognized that the views of FIGS. 2 through 5 are greatly enlarged to exhibit the features of the cutter element.

With continued reference to FIG. 1A, there is illustrated a blood vessel such as an artery or vein and it is indicated generally by number 24. The blood vessel is shown as being occluded by a fatty deposit (atheroma) 26.

For applying the rotational and translational motion to the drive tube 16 and for inflating and deflating the balloon 20 while aspirating blood and tissue deposits during the course of the atherectomy procedure, there is connected to the proximal end of the catheter a generally tubular housing 28 which is dimensioned to be conveniently grasped in the palm of the hand. Contained within the tubular housing 28 is a motor 30 which is preferably air driven but which alternatively may be electrically powered. The motor 30 has a shaft 32 which is keyed to a rotary union or valve member 34 contained within a valve housing 36. An annular groove 38 is formed in the rotatable union member 34 and disposed on opposed sides of the annular groove 38 are air seals 40 and 42 in the form of O-rings. A bore is formed through the side wall of the valve housing 36 and a fitting 44 fits within that bore for coupling it to a vacuum system (not shown).

The rotatable union member 34 is hollow and the annular recess 38 is ported to the hollow interior thereof by a radial bore (not shown). A coupler 46 is used to join the rotatable union 34 to the drive tube 16. Thus, by this arrangement, when the motor 30 is energized, the tubular drive member 16 is rotated within the lumen of the intermediate tube 14 and, simultaneously, a suction may be applied to the lumen of the drive tube 16 to draw blood and any tissue debris back to the proximal end of the assembly.

A fluid port 48 is also formed through the side wall of the tubular plastic housing member 28 and it communicates with a chamber 49. This chamber is adapted to be filled through port 48 with a suitable fluid such as saline solution and provides the means whereby the balloon or expander member 20 may be inflated. More particularly, the lumen of the outer tube 12 is open to the interior of the chamber 49 through compression fitting 50 and when the hydraulic pressure is appropriately increased, the saline solution flows into the expander member 20 to cause it to inflate to its maximum, predetermined outside diameter. By applying a negative pressure to the port 48 the inflation medium can be aspirated out from the proximal end of the outer tubular member 12 causing the expander member 20 to assume its low profile condition of being collapsed against the periphery of the intermediate tube 14. Again, an O-ring seal 52 is used to preclude the flow of liquid beyond the rotary union housing 36.

To effect translational or longitudinal movement of the cutter 22 relative to the distal end of the intermediate tube 14, there is provided on the housing 28 a thumb grip 54 having a stem 56 passing through an elongated slot 58 formed in the tubular housing 28. The stem 56 may be affixed to the motor assembly 30 which slidingly fits within the lumen of the tubular housing 28 or alternatively to the rotary union housing 36. Thus, by pushing on the thumb grip 54, the motor 30 and the rotary union 36 can be moved back and forth within the bore of the tubular housing 28.

Referring to FIGS. 2 through 4, there is shown an enlarged view of the distal end portion of the working catheter 16. As can be seen, it includes a plurality of fibers 23 anchored to the exterior of the tube 16 at one end only thereof. More particularly, the fibers 23 are shown as being adhesively or thermally bonded at 25 to the exterior of the tube 16. While in FIG. 2 it is the distal end of each of the fibers 23 that is bonded to the exterior of the tube 16, it is to be understood that the invention will work just as well when the opposed end of each of the fibers is the bonded end.

The connection between the individual fibers 23 and the outer surface of the working catheter 16 is such that the fibers tend to lay flat against the side wall of the catheter. However, when the drive motor assembly 30 is energized to rotate the drive or working catheter 16 at a high rotational velocity, centrifugal force causes the individual fibers 23 to stand erect as shown in FIG. 3 to flail and pulverize the stenotic lesion 26.

FIG. 5 shows an alternative arrangement for the cutting tip in accordance with the present invention. Here, rather than having discrete monofilament fibers bonded to the exterior of the tube as in the embodiment shown in FIGS. 2 through 4, the flailing fingers are integrally formed in the wall of the tube 16 by creating a series of U-shaped slits 60 to define fingers 62. As with the embodiment of FIG. 2, when the working catheter 16 is spun at high speed, centrifugal force will cause the fingers 62 to project radially out forming tiny whips which flail and disintegrate the stenotic lesion.

OPERATION

FIGS. 1A, 1B and 1C are included to illustrate the preferred mode of operation of the atherectomy catheter of the present invention. As indicated in FIG. 1A, the catheter assembly with the cutter 22 retracted is advanced up over a guidewire to the occlusion 26 within the blood vessel 24. At this point, saline or other suitable inflation fluid is injected through the port 48 into the chamber 49 and, thence, through the lumen of the outermost tube 12 to inflate the expander member 20. This action stabilizes the tip end of the catheter assembly and inhibits relative movement between the outer tubular member 12 and the blood vessel 24. Next, and as represented by FIG. 1B, the motor 30 is energized to drive the cutter tube 16, and at the same time, the surgeon may, by pressing on the thumb grip 54, advance the rotating cutter tip over the guidewire and into the lesion 26. While this procedure is taking place, a vacuum is preferably applied, via port 44 and the rotary valve member 34, to the lumen of the drive tube 16 whereby blood and other debris cut loose during the procedure is sucked back through the lumen of the drive tube and into a suitable receptacle (not shown).

Once a path has been cut into the lesion 26, the expander member 20 may be evacuated to collapse it to its smallest diameter and then by advancing the entire catheter assembly 10 further in the distal direction, the expander 20 is made to enter the previously cut opening in the lesion.

Following that, the expander may again be inflated and the steps repeated until such time as the balloon is made to pass completely through the occlusion to spread it open and to restore patency to the blood vessel 24.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. An atherectomy catheter for removing atheromas from a blood vessel wall comprising:
   (a) an elongated flexible tubular shaft having a proximal end and a distal end, said shaft including a plurality of fibers of a predetermined length with only one end of each constrained by attachment to the outer surface of said shaft and normally extending parallel thereto proximate a portion of said distal end; and
   (b) means for rotating said shaft at a sufficiently high speed to cause said fibers to project radially outward of said shaft due to centrifugal force for flailing said atheroma and disintegrating same.

2. The atherectomy catheter as in claim 1 wherein said plurality of fibers are integrally formed on said shaft by forming a pattern of slits through the wall of said tubular shaft.

3. The atherectomy catheter as in claim 1 wherein said plurality of fibers comprise monofilament members of a predetermined length bonded at one end only thereof to said tubular shaft.

4. A method of conducting an atherectomy procedure comprising the steps of:
   (a) advancing a balloon tipped tubular guide catheter containing a coaxially disposed and axially moveable drive tube with a cutter member attached to its distal end through the vascular system to the site of the atheroma to be treated, said cutter comprising a plurality of filaments adhered to said drive tube at only one end of said filaments;
   (b) inflating the balloon on said tubular guide catheter;
   (c) rotating said drive tube and cutter at a predetermined speed sufficient to cause said plurality of filaments to project radially from said drive tube while advancing said drive tube beyond the distal end of said guide catheter and into said atheroma;
   (d) during step (c), applying a vacuum to the proximal end of said drive tube for aspirating blood and tissue matter through the lumen of said drive tube;
   (e) deflating said balloon; and
   (f) repeating steps (a) through (e) until said balloon passes completely through the atheroma.

5. An atherectomy catheter assembly comprising:
   (a) a first, flexible tubular member of a predetermined outside and inside diameter having a proximal end, and distal end and a lumen extending from said proximal end to said distal end;
   (b) an inflatable expander member attached to said distal end of said first tubular member to be inflated by fluid passing through said lumen of said first tubular member;
   (c) a second tubular member having an outer diameter less than said predetermined inside diameter of said first tubular member, a proximal end, a distal end, and a lumen extending from said proximal end to said distal end of said second tubular member, said second tubular member being coaxially disposed within said lumen of said first tubular member with a predetermined clearance between said outer diameter of said second tubular member, allowing rotation and axial displacement of the distal end of said second tubular member beyond the distal end of said first tubular member;
   (d) a cutter member attached to said distal end of said second tubular member, said cutter member including a plurality of filamentary strands having one end thereof adhered to said distal end of said second tubular member and normally extending parallel to the axis of said second tubular member;
   (e) motor means coupled to said proximal end of said second tubular member for imparting rotation thereto within said lumen of said first tubular member;
   (f) means coupled to said proximal end of said first tubular member for directing fluid through said lumen of said first tubular member to inflate and deflate said expander member;
   (g) means for applying a negative pressure to said lumen of said second tubular member at the proximal end portion thereof; and
   (h) means located at said proximal end of said second tubular member for axially extending and retracting said distal end of said second tubular and said cutter member from said distal end of said first tubular member as said second member is being rotated by said motor means, rotation of said second tubular member causing said filamentary strands to project radially from said second tubular member.

* * * * *